United States Patent [19]

Heilman et al.

[11] 4,291,707
[45] Sep. 29, 1981

[54] IMPLANTABLE CARDIAC DEFIBRILLATING ELECTRODE

[75] Inventors: Marlin S. Heilman, Gibsonia; Alois A. Langer, Pittsburgh, both of Pa.

[73] Assignee: Mieczyslaw Mirowski, Owings Mills, Md.

[21] Appl. No.: 34,730

[22] Filed: Apr. 30, 1979

[51] Int. Cl.³ .............................................. A61N 1/04
[52] U.S. Cl. .............................. 128/784; 128/419 D; 128/798
[58] Field of Search ............... 128/642, 419 D, 419 P, 128/784, 785, 798, 799, 802

[56] References Cited

U.S. PATENT DOCUMENTS

| | | | |
|---|---|---|---|
| 3,244,174 | 4/1966 | Wesbey et al. | 128/419 P |
| 3,386,445 | 6/1968 | McDonald | 128/798 |
| 3,815,611 | 6/1974 | Denniston | 128/419 D |
| 4,011,861 | 3/1977 | Enger | 128/419 P |
| 4,030,509 | 6/1977 | Heilman et al. | 128/419 D |
| 4,146,037 | 3/1979 | Flynn et al. | 128/419 P |

*Primary Examiner*—William E. Kamm
*Attorney, Agent, or Firm*—Fleit & Jacobson

[57] ABSTRACT

Disclosed is an implantable cardiac electrode for use in defibrillation. The electrode has a metallic mesh electrode surface surrounded by an insulating material which is formed so as to increase the metallic surface area while providing a substantially uniform current density across the electrode surface. An additional electrode tip is included for use in the event that pacing is required; the pacer tip may have a detachable lead for removal after surgery. The electrode may be implanted without major surgery by means of a specialized insertion tool which cooperates with a pocket formed in the electrode. After implantation, the electrode may also be used as a pick-up in an electrocardiogram system.

21 Claims, 11 Drawing Figures

IMPLANTABLE CARDIAC DEFIBRILLATING ELECTRODE

BACKGROUND OF THE INVENTION

It is well known that cardiac arrhythmias, such as atrial or ventricular fibrillation, can be overcome by applying electrical energy to the fibrillating myocardium. This procedure, defibrillation, can be accomplished by applying the electrical energy either to the chest of the patient by means of conductive-metal paddles held in place by medical personnel or, during the course of cardiac surgery, by holding conductive-metal paddles in direct contact with the surface of the heart. Such procedures are well known and have been found to be generally effective.

More recently, implantable defibrillators have been proposed for automatically detecting the onset of the cardiac arrhythmia and for automatically correcting such arrhythmia. These automatic defibrillators may employ conformal electrodes, which are maintained in contact with the surface of the heart or, electrodes on an intravascular catheter, or some combination of these. In any case, the electrodes act to impart the desired electrical energy to the heart muscle to achieve defibrillation.

With the intravascular catheter electrode approach, it has been found that although less electrical energy need be imparted to the heart than in the exterior chest paddles approach, more energy is needed than in the system wherein the electrodes are placed directly in contact with the heart surface. In other words, it has been found that physically placing the electrodes in contact with the exterior of the heart will provide a more efficient use of the electrical energy, thereby reducing the amount of energy required. Obviously, energy consumption is of the utmost importance in any implanted medical-electronic device.

In the automatic defibrillators, previously under consideration, the defibrillation electrodes have been designed for application to the heart by entering the chest cavity and by sewing the electrodes to the heart or positioning the electrodes on the surface of the heart. At times, such electrode implantation may be accomplished during the course of cardiac surgery, such as during a bypass operation. However, even when such heart surgery is not independently required, the previous surface electrodes required that the chest cavity be opened in order to implant the defibrillating electrodes. This surgical procedure requires intubation of the lungs and exposes the surfaces of the lungs to possible infection. Additionally, in order for the surgeon to have sufficient working space to effectively position and apply the electrodes, it may be necessary to perform an additional surgical procedure involving spreading two adjacent ribs or splitting the sternum. Accordingly, at the present time, in order to apply any type of cardiac electrodes to the surface of the heart, it is necessary to perform major surgery. Nevertheless, it is desirable to be able to implant the electrodes without the necessity of entering the pleural space, thereby maintaining the integrity of the pleural cavity.

Moreover, known surface electrodes suffer from the disadvantage that less than uniform energy density results from a discharge. Higher energy densities appear at the electrode edges, and at higher discharge levels, damaged tissue could result at the heart surface. It is, of course, desirable that the discharge be uniform over the entire electrode surface and that no regions of high energy density be present.

SUMMARY OF THE INVENTION

The present invention is generally related to the field of electrical defibrillation and, more specifically, to particular cardioverting electrode configurations for use in implantable defibrillators, as well as to methods for the implantation of such electrodes.

"Cardioverting" or "cardioversion" as used herein is intended to encompass the correction of a number of arrhythmic heart conditions, both lethal and nonlethal. Those arrhythmic heart conditions include atrial tachycardia, atrial flutter, atrial fibrillation, junctional rhythms, ventricular tachycardia, ventricular flutter, ventricular fibrillation, and any other non-pacemaking related arrhythmic condition which may be corrected by applying electrical shocks, which are of a magnitude substantially greater than pacing shocks, to the heart. Obviously then "defibrillation" is included in the term cardioversion as a method of applying electrical shocks to the heart to defibrillate fibrillating atria or fibrillating ventricles.

In one embodiment, the cardioverting electrode is of rectangular shape which is designed for insertion through the soft tissues outside the pleural cavity and then to be arranged in contact with the heart. The electrode has a specific configuration which enhances energy efficiency, while providing optimum transfer of electrical energy to the heart, and preventing high-current densities from existing at the edges of the electrode.

The electrode is formed of a metallic mesh or screen which is sandwiched between two layers of a chemically inert, electrical insulation material. In this manner, the portions of the electrode facing away from, i.e., not in contact with the heart surface, are electrically insulated from the body. An alternative, yet a somewhat less efficient, embodiment is to use only a single layer of insulation on the back and to stitch such layer to the screen. The defibrillation electrode may be provided with an additional electrode, which is utilized to provide a cardiac pacing function. Means are also provided to permit disconnection of the electrical lead to the pacing tip, after the surgical implantation has taken place, at such time when it may be reasonably assumed that cardiac pacing is not required.

Additionally, the inventive electrode may also be used as a pick-up electrode in an electrocardiogram (ECG) system to detect the electrical activity of the heart. Since both functions need not occur simultaneously, the same electrical lead can be used both in the defibrillator function and in the ECG function.

Implantation of the electrode by the inventive method consists of the steps of first making a skin incision on the interior thoracic or abdominal wall, and then positioning the electrode on the surface of the heart by using a hand-held instrument to separate the tissue planes and to create a tunnel inside the thorax, but outside the pleural cavity, through the soft tissues surrounding the heart. Upon creating the tunnel, one or more electrodes may be placed into the tunnel and arranged proximate the surface of the heart. In one embodiment, two electrodes are placed on opposing sides of the heart and means are provided whereby the proximal ends of the electrodes may be sutured to the adjacent tissue, in order to provide positive electrode fixation. In another manner of practicing the inventive method, a first tunneled space is located between the interior surface of the sternum and the exterior surface of the heart's pericardium, and a second tunnel is created on the heart's inferior surface between the pericardium and the diaphragm.

In order to perform the inventive method described above, a specialized inventive implantation tool is provided which cooperates with the electrode being implanted to permit relatively easy placement of the electrode in relation to the heart and subsequent withdrawal of the implantation tool.

In one embodiment of the electrode, the edge surface of the electrode is constructed so as to have a higher impedance to current flow than the central portion, thereby providing efficient, and relatively uniform, energy transfer by eliminating the so-called "edge effect". Such impedance is controlled by the use of a mechanically embodied electrical filter having spaced holes located over the edges of the mesh electrode.

It is, therefore, one object of the present invention to provide defibrillating electrodes, which are highly efficient in transferring electrical energy to the heart.

Another object of the present invention is to provide defibrillator electrodes, which minimize any electrical damage that may be done to the heart muscle during defibrillation.

It is a further object of the present invention to provide a defibrillation electrode, which may be implanted and arranged next to the heart in a manner requiring only a minimum amount of surgery.

Still another object of the present invention is to provide a defibrillation electrode which also has a pacing tip.

It is yet another object of the present invention to provide an electrode which may be used both as a defibrillation electrode and as a pick-up electrode for ECG signals.

Another object of the present invention is to provide a method for implanting a defibrillator electrode adjacent to the heart without the need for major surgery.

A further object of the present invention is to provide a method for inserting electrodes into the body by making only a skin incision and utilizing a specialized tool to create a tunnel inside the thorax but outside the pleural cavity.

It is still a further object of the present invention to provide a specialized tool for use in inserting the inventive electrode by means of the inventive method.

Yet another object of the present invention is to provide a defibrillating electrode having a heart-pacing tip wherein the lead connecting the pacing tip to the pacing apparatus, located externally of the patient, is provided with a separable connector so that after surgery a temporary pacing lead may be disconnected and removed.

It is another object of the present invention to provide an implantable defibrillation electrode having a specialized receiving pocket at its forward-most end to receive the leading edge of an implantation tool, which will permit insertion of the electrode through the soft tissues of the thorax, while permitting the insertion tool to be withdrawn after placement of the electrode.

The manner in which these and other objects are accomplished by the present invention, as well as the many attendant advantages thereof, will become more readily apparent when reference is made to the following description, taken in conjunction with the accompanying drawings.

DETAILED DESCRIPTION OF THE DRAWINGS

Figure 1:
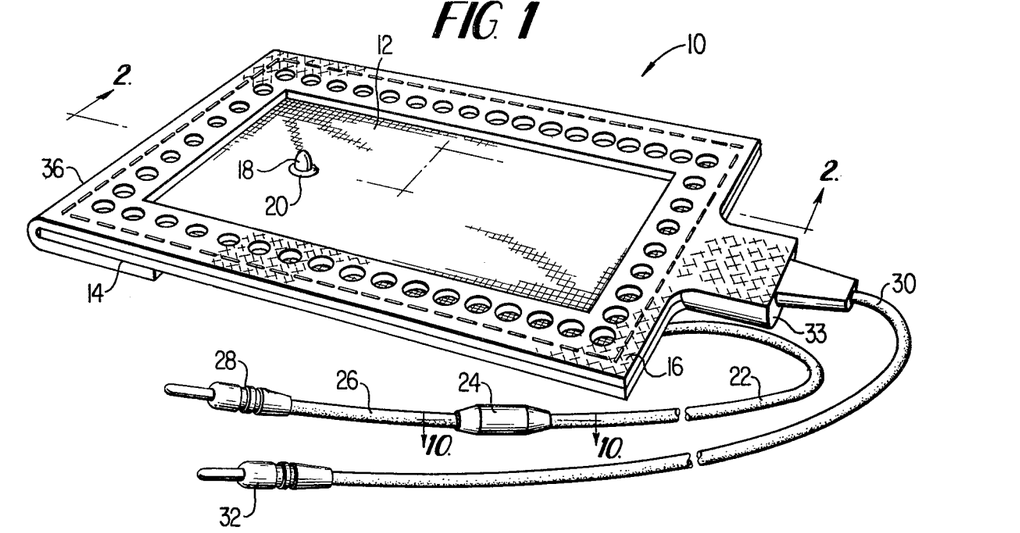
FIG. 1 is a perspective of the inventive electrode.

Referring first to FIG. 1, the inventive electrode 10 is formed in a substantially rectangular configuration, with side dimensions ranging from approximately 1.5 to 4 cm and 3 to 6 cms, respectively. Preferably, the electrode 10 is approximately 4×6 cm. In special cases the electrode may also be formed as a square. The actual metallic electrode element is a mesh or screen 12, which may be formed of titanium or platinum. Alternately, the electrode may be formed of expanded platinum. The mesh is a 150 mesh, having 150 elements or individual wires per inch. The wire diameter is chosen to be between 1 and 3 mils. The electrode mesh 12 is first prepared by spot welding together the wires located around the periphery of the mesh. After spot welding, the excess lengths of wires are then ground or machined flush, so as to produce a smooth edge and to form a continuous border.

The body of the electrode may be formed of two layers of Silastic with the metallic electrode element sandwiched therebetween. The electrode 10 is formed by providing a first bottom layer 14 then applying the titanium mesh 12 and, finally, having a top layer 16 and applied thereupon. The thickness of the assembly should be approximately 1 to 3 cm. The top layer 16 has a rectangular aperture cut into it so that the titanium mesh 12 may make electrical contact with the surface tissue of the heart. In order to provide structural strength, a reinforcing mesh of Dacron may be embedded in both of the Silastic layers and, at the very least, should be used in the bottom layer 14.

The inventive electrode 10 may also be provided with a pacing button 18, which is centrally arranged in the metal mesh 12, and which is electrically insulated from the mesh 12 by means of a suitable insulator 20. The pacing button 18 may be formed of platinum or some other suitably inert conductor. The pacing button 18 should extend approximately 1 to 3 millimeters above the surface of the titanium mesh 12. The electrical lead for the pacing button 18 is seen at 22 and is provided with a specialized detachable coupler 24, located at the end of the conductor 22. The detachable coupler 24 will be further described and shown in more detail hereinbelow. Issuing from this connector 24 is another conductor 26 which is connected to a suitable plug 28 for connection to the appropriate electronic cardiac pacing apparatus. Upon implanting the electrode 10, the conductor 26 is arranged externally to the patient with the coupler 24 located just inside the skin of the patient. In this way, if necessary following surgery, the lead 26 is available to make a connection for the heart pacing function. Subsequently, after the patient's condition has been stabilized, and when it appears to the physician that the pacing function will not be required, the lead 26 may be pulled from the coupler 24 with no additional surgical procedures required.

The mesh 12 of the electrode 10 is connected to the proper source of electrical current through an insulated cable 30 having a suitable electrical connector 32 located at one end. The other end of the cable 30 is electrically connected to the mesh 12 at a low resistance joint located inside an insulated boot 33.

As stated above, it is an object of the present invention to provide an energy efficient electrode which does not require creating large incisions or openings in the thorax, in order to effect direct surgical placement of the electrodes. It is also another object of the present invention to construct such electrodes so as to minimize the possibility of any damage to the heart caused when using the electrode for defibrillation. In this regard, it has been found that when employing defibrillation electrodes having opposed conductors, as contemplated by the present invention, there is present in the electric field between these two conductors a phenomenon commonly associated with parallel plate capacitors, to wit, the edge effect. Briefly stated the edge effect involves the electric field between two plates of a capacitor wherein the electric field is normal to the plates except near the plate edges, at which place the electric-field lines tend to bulge outwardly. These bulging field lines which are concentrated near the edges of the capacitor plates (in the present case they are located near the edges of the titanium mesh) produce a higher current density than that which is present over the central portion of the metal electrode surface.

In order to eliminate the adverse effects of higher current densities due to the edge effect, as well as to simultaneously maximize the surface area available to reduce the current densities over the metallic electrode surface, the present invention provides a plurality of holes, which are cut through the top layer 16 of Silastic down to the surface of the mesh 12, in the vicinity of the edges of the mesh. These holes are shown typically at 34 in FIG. 1 and, as may be seen, the surface of the margin of the titanium mesh screen 12 is exposed therethrough. It has been found that by means of these holes 34, the edge effect which creates high current densities can be substantially eliminated and also that the mesh 12, which shows through the holes 34, increases the surface area of the electrode which is available to contact the heart surface, thereby also tending to lower the current densities on the metallic electrode elements.

The two layers and the metallic mesh may be securely fastened together by placing stitches 36 around the periphery of the electrode 10 with a conventional sewing machine using Dacron thread or the like.

The leads 22, 30 are preferably formed of a special, extremely flexible, electric cable, which is particularly suitable for use with implanted cardiac electrodes. Such flexibility is extremely important so as to permit cardiac activity without trauma. This cable is commonly known as tinsel and is formed having a central strand of a polyester yarn and around such central strand are wound six or more conductive strands of silver. Each conductive strand comprises, in turn, its own polyester yarn core and concentrically wound conductive strands. This tinsel wire has an exceedingly long life in the face of mechanical stress, such as flexure. Additionally, since it is formed of silver, the tinsel wire has an extremely low electrical resistance. The tinsel wire cable 30 must be electrically connected to the titanium mesh 12 and this operation is accomplished on the bottom surface of the mesh by crimping, welding, or some other similar electrical connecting operation. Alternately the cable 30 may be attached to the mesh 12 by means of a specialized clip which is described in copending application, Ser. No. 34731, entitled Device and Method for Making Electrical Contact.

Figure 2:
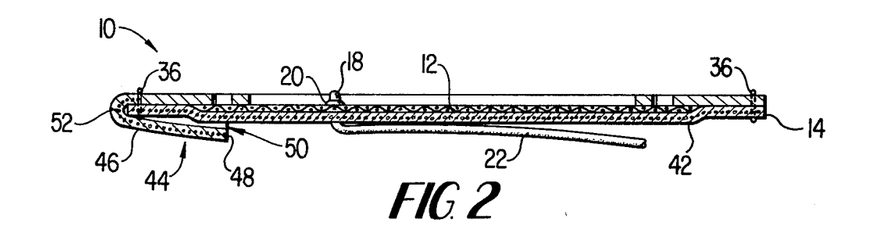
FIG. 2 is a cross section through the electrode of FIG. 1 taken along sight line 2—2.

Turning now to FIG. 2, the arrangement of the various elements making up the electrode 10 of FIG. 1 is shown in cross section, taken along sight line 2—2 of FIG. 1. In such cross section, the top Silastic layer 16 is bonded to the bottom Silastic layer 14 and the titanium mesh electrode 12 is sandwiched therebetween. It is seen that the holes 34 expose an additional surface area of the mesh 12 to the heart surface. The pacing tip 18 is connected to its flexible cable 22 and the tip 18 is electrically insulated from the mesh 12 by means of an insulator 20.

Also seen in the cross section of FIG. 2 is a layer of Dacron mesh which may be utilized as a strengthening element in either or both Silastic layers of the sandwich. In this embodiment the mesh is placed in the lower layer 14 and is seen in cross section at 42 and at the leading edge of the assembly where stresses occur during implanting. Similar Dacron mesh could also be used to strengthen the top layer 16. The specialized pouch or pocket arrangement 44 which interacts with the specialized insertion or implantation tool, for placement of the electrode 10 with minimum surgical involvement, is shown in cross section also. The pocket or pouch 44 is formed by continuing the top layer 16 of Silastic down over the leading edge of the electrode so as to form a lip 48 which extends parallel to the bottom layer 14 of the electrode, thereby forming a pocket 50 across the entire width of the electrode to receive the insertion tool. Additionally, a portion of Dacron mesh 52 may be embedded in the pocket or pouch 44 in order to provide added strength to the pocket to prevent tearing by the insertion tool.

Figure 3:
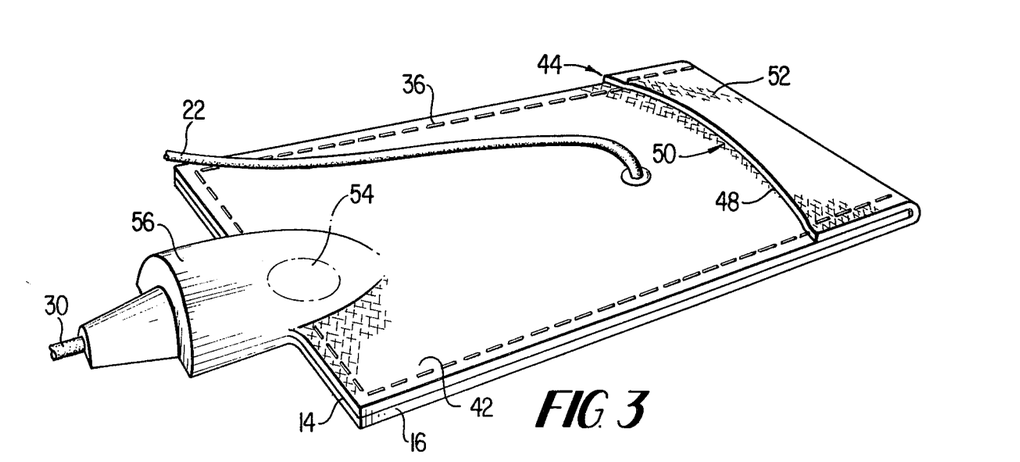
FIG. 3 is a perspective of the bottom surface of the inventive electrode of FIG. 1.

FIG. 3 is a perspective from the bottom of the inventive electrode 10 and in this view the pocket arrangement 44 is seen in more detail. Also seen in FIG. 3 is the Dacron mesh 42, which is embedded inside the bottom Silastic layer 14. The specialized pocket 44, which is intended for use during insertion of the inventive electrodes, is raised above the bottom layer 14 so as to form the desired pocket 50. The opening of the pocket 50 must be directed backwards and opening towards the rear of the electrode, for reasons which will become clear below. The additional Dacron mesh strengthening layer is seen at 52. The location of the joint between the electrical conductor 30 and the wire mesh 12 is in the area shown generally at 54 and, after such suitable electrical connection, the boot 33 is placed over the joint area to provide both electrical insulation and mechanical strain relief.

Figures 4, 5:
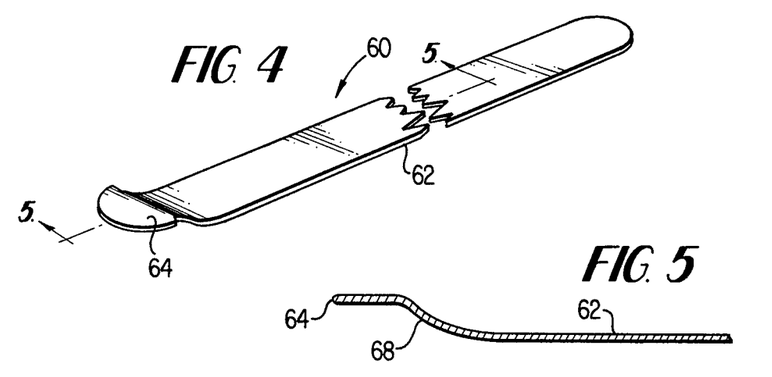
FIG. 4 is a perspective of a tool suitable for inserting the inventive electrode.
FIG. 5 is a cross section of the insertion tool of FIG. 4 taken along plane 5—5.

The inventive method for implanting the present defibrillation electrode and pacer tip will be set forth below, however, preliminarily thereto it is necessary to show and describe a preferred embodiment of a suitable insertion tool for use in practicing such inventive method. FIG. 4 shows a perspective view of a preferred embodiment of the insertion tool which is formed essentially as an elongated, flat, mandrel-type probe 60. The probe 60 has an elongated flat handle portion 62 and a blunt but rigid leading edge 64 which is utilized to form a tunnel through the soft-tissue plane during the electrode insertion process. The plane of the handle 62 changes somewhat to form the upraised leading edge 64.

FIG. 5 is a cross section of a portion of the insertion tool 60 of FIG. 4 and shows the location of the upraised leading edge portion 64, in relation to the plane of handle 62. The leading edge portion 64 is provided to interact with the pocket 50 formed in the bottom surface of the electrode 10 and, as may be seen by comparing FIGS. 2 and 5, in such interaction portion 64 will slide easily into the pocket 50 in one direction and the electrode will then lie parallel the plane of the handle 62. Accordingly, the relative motion which is possible between the insertion tool 60 and the electrode 10 is unidirectional. After insertion of the electrode, the tool 60 is withdrawn, thereby permitting the leading edge portion 64 to slip out of the pocket 50, while the electrode is retained in place next to the heart. Additionally, upon insertion of the leading edge portion 64 into the pocket 50 of the electrode 10, the electrode itself becomes part of the means for insertion into the human body.

Figure 6:
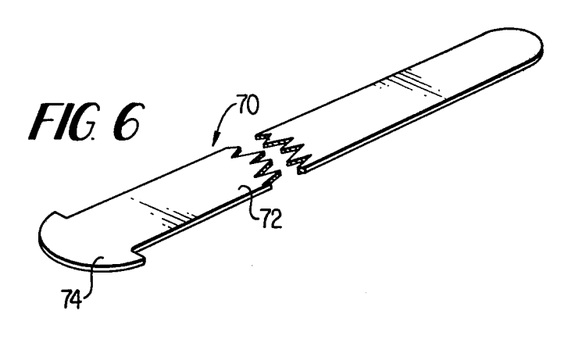
FIG. 6 is a perspective view of another embodiment of a tool suitable for inserting the inventive electrode.

FIG. 6 shows another embodiment of an insertion tool 70, which has an elongated handle portion 72 and a leading edge portion 74. The leading edge portion 74 is inserted into the pocket 50 in the electrode. This insertion tool 70 is formed as a planar instrument.

As described above, it is an object of the present invention to provide a method of implanting a defibrillation electrode system by making only a skin incision, i.e., not involving major chest surgery, on either the interior thoracic or abdominal wall. Hence, by means of a specially provided hand-held instrument, the tissue planes are separated and a tunnel is created inside the thorax but outside the pleural cavity through the soft tissues which surround the heart. After forming a tunnel, one or more electrodes may be inserted into the tunnel and arranged proximate the surface of the heart. The present invention contemplates the forming of one tunnel between the interior surface of the thorax and the exterior surface of the heart's pericardium and, attendantly, the insertion of one or more electrodes through such tunnel for ultimate placement proximate the heart. Additionally, the present invention teaches another tunnel created on the posterior surface of the heart's pericardium, between the pericardium and the diaphragm, and also placement of cardiac electrodes through this second tunnel.

Figures 7, 9:
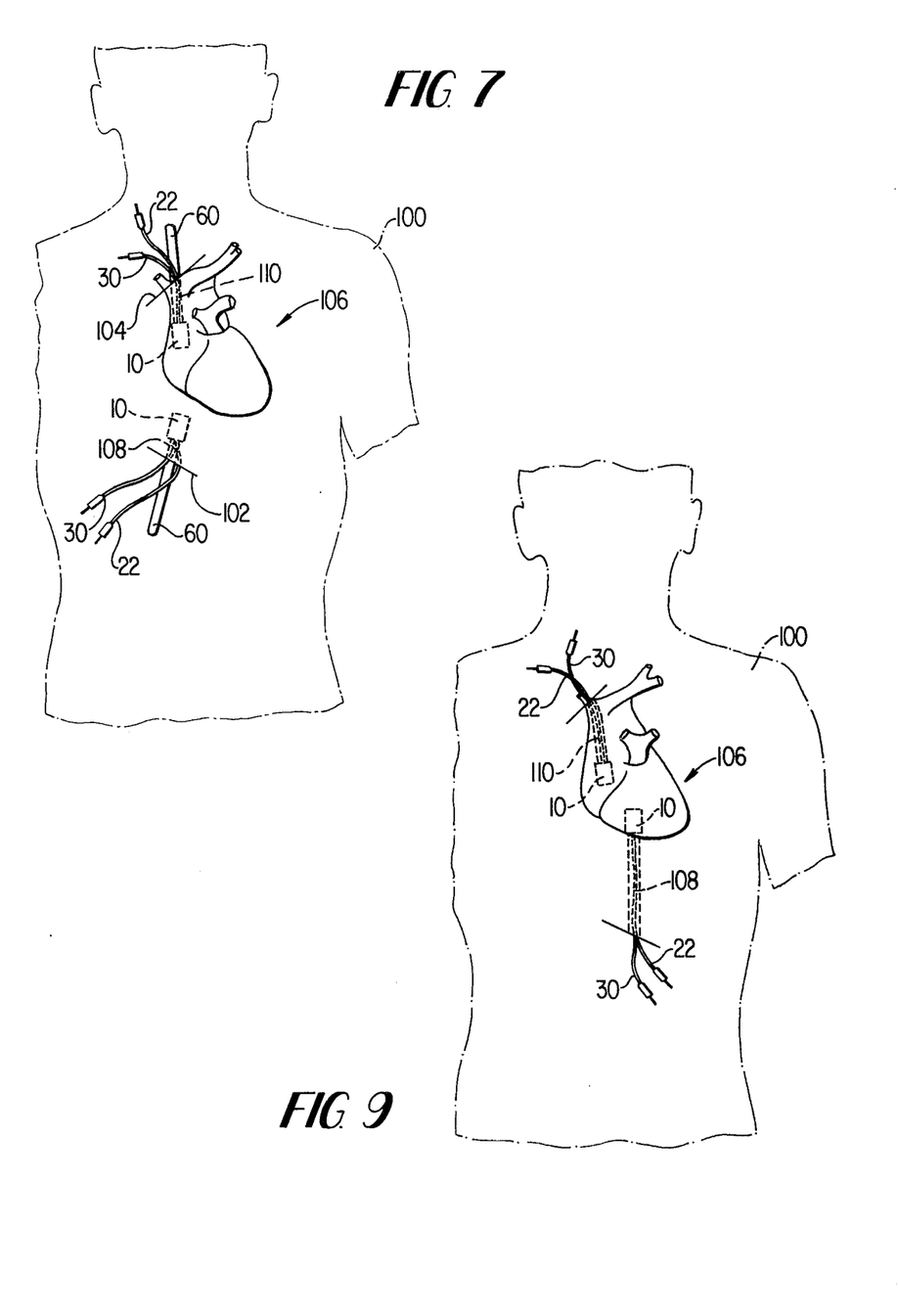
FIG. 7 is a schematic representation showing the insertion of the inventive electrode into the body.
FIG. 9 is a perspective of the inventive electrode arranged on the insertion tool prior to implantation of the electrode.

Turning to FIG. 7, the silhouette of the thoracic region of a patient 100 is shown and the incision locations are shown at 102 and 104. In the silhouette of FIG. 7 the location and general outline of the patient's heart is seen at 106. In regard to the abdominal incision 102, whereat the incision tool 62 may be seen partially protruding through this incision, the tunnel is being created which is located on the inferior surface of the heart's pericardium between the pericardium and the diaphragm. The inventive electrode 10 is shown in position and retained on the insertion tool 60. The two leads 22 and 30 are also shown protruding from the incision 102.

Figures 8, 10:
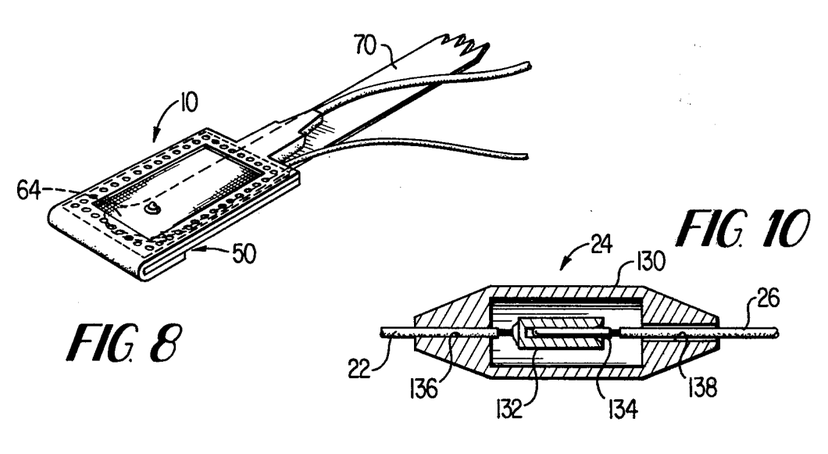
FIG. 8 is a schematic representation showing another manner of insertion of the inventive electrode into the body.
FIG. 10 is a cross-sectional view of the separable coupler utilized in the embodiment of FIG. 1.

Referring for a moment to FIG. 8, the inventive electrode 10 is shown installed on the specialized insertion tool 60 and the leading edge 64 of the insertion tool 60 having been inserted into the pocket 50 formed in the back surface of the inventive electrode 10. As may be seen in phantom, the leading hard edge 64 of the insertion tool 60 is at the front of the electrode 10. During insertion through the soft tissue planes, the electrode 10 and the hard leading edge 64 of the insertion tool cooperate to form the tunnel.

Referring back to FIG. 7, it may be seen that the tunnels are being formed as indicated above. In relation to the upper incision 104, which is made in the interior thoracic region, a tunnel 110, similar to 108, is being created between the interior surface of the thorax and the anterior surface of the heart's pericardium and the handle 62 of the insertion tool 60 is shown protruding through the incision 104, as are the leads 22 and 30.

In FIG. 9, it may be seen that by completely inserting the insertion tool 60 and tunnels 108 and 110 are fully formed, and upon withdrawing the insertion tool 60, the leading edge portion 64 of the tool slips out of the pocket 50 of the electrode 10 and the electrode remains at its original location. FIG. 9 shows the electrodes in place after having been inserted through the tunnels formed in the soft tissue planes and after having the insertion tool withdrawn from the tunnels. In FIG. 9, the leads are shown extending through the incisions; however, these leads will be ultimately disposed of in accordance with the desired outcome, i.e., whether or not pacing is required and whether or not the defibrillator is of a completely implanted type.

There are also other procedures which may be followed in applying the inventive electrodes to the heart and the apparent order of combination preferences might be as follows. A superior vena cava electrode in combination with a tunneled diaphragmatic electrode. Another combination might be a substernal patch in combination with a diaphragmatic patch, wherein both electrodes were introduced via a subziphoid route. Of course, the locations as shown in FIG. 9 are another combination.

FIG. 10 is a cross sectional view of the inventive releasable lead coupling, shown at 24 in FIG. 1. As mentioned above, this type of coupling is intended for use with the pacer tip so that after implantation of the present electrode an electrical connection is available for quick hook-up to a heart pacing device so that if necessary, cardiac pacing may be easily and quickly achieved. The inventive coupling is provided so that when it becomes clear that cardiac pacing will not be required, the lead may be pulled free, with the coupling remaining in the patient, and no further surgery will be required.

In FIG. 10, an outer casing 130 of the coupling 24 surrounds a female-type metallic connector 132 which is electrically connected to the pacing lead 22. Forming an electrical joint with the female connector 132 is a male plug 134 which is electrically connected by either soldering or crimping to the external pacing lead 26. The casing 130 of the coupling is constructed such that there is a tight mechanical bond formed at 136 between the pacing lead insulation 22 and the casing 130, whereas in the case of the external pacing lead 26, the housing 130 is formed having an excessively large passage, shown typically at 138, which is of greater diameter than the outside diameter of the pacing lead 26. Such greater diameter is provided so that when it is desired to disconnect the external pacing lead, a tensional force may be applied to the external lead 26 so that parts 132 and 134 will be separated, thereby permitting the external lead 26 to be withdrawn from the patient's body.

Figure 11:
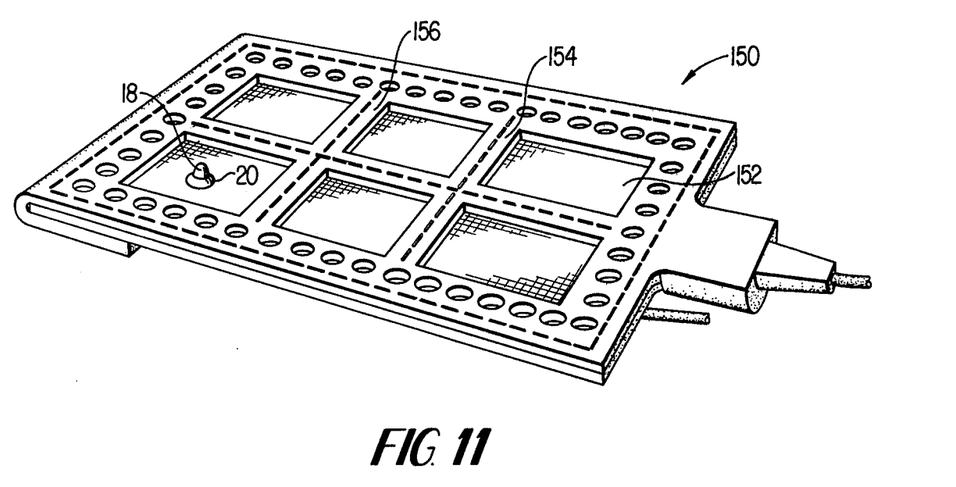
FIG. 11 is a perspective of another embodiment of the inventive electrode.

FIG. 11 shows an alternate embodiment of the inventive electrode. In this embodiment, the electrode 150 is constructed as was electrode 10 of FIG. 1, except that top layer 16 is provided with a plurality of apertures 152 in place of the single large opening. These apertures 152 are formed by crossing members 154 formed in the top layer 14. This multiple aperture embodiment still permits use of the pacing tip 18, which is then relocated in one of the several available apertures.

These cross members 154 and additional stitches 156 have been found advantageous in maintaining the original form and function of the electrode. After implantation of an electrode the tissue adjacent to the metallic mesh has been found to adhere and grow on and through the metallic mesh. When this happens, the tissue gets behind the mesh and tends to force it away from the back layer. This ultimately distorts the electrode shape and degrades its performance by adversely affecting the contact surface. The additional stitches 156 keep the mesh firmly affixed to the back portion.

It is, of course, understood that the above detailed description is intended by way of example only and is not intended to limit the present invention in any way, except as set forth in the following claims.

What I claim is:

1. An implantable cardioverting electrode assembly for placement proximate the heart and for connection to a suitable cardioverting system, the assembly comprising:
    a flexible electrically conductive planar electrode means for placement proximate the heart, said electrode means having an electrically conductive margin defining the outer perimeter of said electrode means and at least one exposed conducting area surrounded by said margin,
    an electrical insulating element covering the surface of said planar electrode facing away from the heart,
    electrical conductor means arranged to electrically connect said electrode means and said cardioverting system, and
    a layer of electrical insulation material arranged on a conductive surface of said margin of said electrode means, which conductive surface is proximate the heart, said layer having at least one open central area to permit the central portion of said electrode means to be exposed and substantially covering the margin of said electrode means, said insulation material having a plurality of small apertures therein located about said margin of said electrode means for also exposing the electrode surface therethrough, whereby said plurality of small apertures substantially eliminates edge effect current concentrations.

2. The assembly of claim 1 further comprising a cardiac pacing electrode arranged on and electrically insulated from the surface of said planar electrode for contacting the surface of the heart, and a manually separable electrical connector having a first contact electrically connected to said cardiac pacing electrode and a second contact electrically connected to a cardiac pacing system located externally to the patient, whereby said pacing electrode can be disconnected from said cardiac pacing system by removing said second contact from said manually separable electrical connector.

3. The assembly of claim 1 wherein said planar electrode is formed of titanium mesh.

4. The assembly of claim 1 further comprising a pocket formed in the back surface of said planar electrode adapted to receive a leading edge of a tool used to implant said electrode assembly.

5. The assembly of claim 1 further comprising a reinforcing mesh embedded in said electrical insulating element to provide added mechanical strength thereto.

6. The assembly of claim 1 further comprising stitching through said planar electrode means, said electrical insulating element, and said electrical insulating material for mechanically binding said assembly together.

7. The electrode of claim 1, wherein said electrical conductor means comprises a silver tinsel electrical cable.

8. An electrode of the type for implantation in a patient for connection to an electrical cardioverting system, said electrode comprising:
    a planar electrical conductor,
    a first layer of electrical insulating material arranged in contact with and entirely covering one side of said planar electrical conductor,
    a second layer of electrical insulating material of substantially the same size as said first layer, having at least one large aperture therein for exposing the central portion of said conductor and covering a perimeter portion of said conductor and having a plurality of small apertures therein located above said perimeter portion for exposing portions of said conductor therethrough, thereby substantially eliminating edge effect current concentrations, and
    flexible electrical conductor means connected to said planar electrical conductor and the electrical cardioverting system, whereby said electrode may be arranged in contact with the heart for effecting cardioversion.

9. The electrode of claim 8 further comprising:
    a pacing electrode for use with cardiac pacing apparatus located externally to the patient, said pacing electrode being located in said planar electrical conductor and being electrically insulated therefrom;
    a manually separable electrical connector having first and second mating contacts;
    a first electrical conductor connecting said pacing electrode and said first mating contact; and
    a second electrical conductor connecting said cardiac pacing apparatus and said second mating contact, whereby upon manually separating said connector, said second mating contact and said second electrical conductor may be removed from the patient.

10. The electrode of claim 8 wherein said planar electrical conductor is formed of titanium mesh.

11. The electrode of claim 10 wherein said titanium mesh is a 150 mesh having a wire diameter between 1 and 3 mils.

12. The electrode of claim 8 wherein said planar electrical conductor is formed of an expanded platinum sheet.

13. The electrode of claim 8 wherein said second layer of electrical insulating material is arranged to extend beyond the edge of the first layer of electrical insulating material opposite the location where said flexible electrical conductor is connected to said planar electrical conductor and being arranged so as to envelop said edge of said first layer, thereby forming an upraised receptacle portion having only one open side on the lower surface of said electrode for receiving a specialized electrode insertion tool.

14. The electrode of claim 8 being formed in a substantially rectangular shape having a width of approximately 4 centimeters and a length of approximately 6 centimeters.

15. The electrode of claim 8 further comprising stitching through said first and second layers of insulating material and said planar electrical conductor for mechanically binding said electrode together.

16. The electrode of claim 8 wherein said at least one large aperture comprises six large apertures separated one from another by cross members formed of said second layer of electrical insulating material.

17. The electrode of claim 8, wherein said first and second layers are distinct parts.

18. The electrode of claim 8, wherein said flexible electrical conductor means comprises a silver tinsel electrical cable.

19. The electrode of claim 8, wherein said first and second layers are formed as a unitary structure from the same piece of insulating material.

20. An implantable flexible planar electrode assembly for placement proximate the heart, said electrode assembly comprising a forward end, a rearward end, a substantially planar surface facing away from the heart, and means overlying a part of said surface defining a rearwardly opening pocket disposed in a plane substantially parallel to and adjacent a plane defined by said surface, said pocket being adapted to cooperate with a placement tool used for implanting said electrode assembly.

21. The electrode assembly of claim 20, wherein said electrode is formed having a layer of electrical insulating material selectively arranged over the surface of said planar electrode, said layer of insulating material being arranged to continue over and around one edge of the electrode to form said pocket having only one open side for receiving said placement tool.

* * * * *